United States Patent [19]
Ross et al.

[11] Patent Number: 5,710,374
[45] Date of Patent: Jan. 20, 1998

[54] ELECTRONIC VISCOMETER

[75] Inventors: Robert A. Ross; James J. Kauzlarich, both of Charlottesville, Va.

[73] Assignee: University of Virginia Patent Foundation, Charlottesville, Va.

[21] Appl. No.: 669,949

[22] Filed: Jun. 25, 1996

Related U.S. Application Data

[63] Continuation-in-part of Ser. No. 418,112, Apr. 6, 1995, Pat. No. 5,571,952.
[51] Int. Cl.⁶ ................................................. G01N 11/10
[52] U.S. Cl. ............................................ 73/54.24; 73/54.26
[58] Field of Search .............................. 73/54.24, 54.25, 73/54.26, 54.27, 54.28, 54.23, 54.39, 54.41

[56] References Cited

U.S. PATENT DOCUMENTS

| | | | |
|---|---|---|---|
| 3,062,040 | 11/1962 | McKennell et al. | 73/59 |
| 3,587,295 | 6/1971 | Simons | 73/64.1 |
| 4,922,745 | 5/1990 | Rudkin et al. | 73/32 A |
| 5,571,952 | 11/1996 | Kauzlarich | 73/54.24 |

Primary Examiner—Hezron E. Williams
Assistant Examiner—Jay L. Politzer
Attorney, Agent, or Firm—Oblon, Spivak, McClelland, Maier & Neustadt, P.C.

[57] ABSTRACT

An electronic viscometer having a vibrating drive in a hollow probe which oscillates along its longitudinal axis and is damped by a sample into which the probe is inserted. The viscometer has a piezoelectric crystal having a feedback electrode, a phase locked loop circuit to track the resonant frequency, drive amplifiers and buffers, and a phase compensation network to ensure that the proper phase relationship is maintained between piezoelectric drive and feedback signals.

8 Claims, 3 Drawing Sheets

ELECTRONIC VISCOMETER

This is a continuation-in-part of application Ser. No. 08/418,112 filed on Apr. 6, 1995 now U.S. Pat. No. 5,571,952.

BACKGROUND OF THE INVENTION

1. Field of the Invention

The present invention relates to an electronic viscometer for measuring the viscosity of fluids.

2. Discussion of the Background

Sample viscosity is often a critical parameter in the paint industry, food industry, pharmaceutical and cosmetic industry, plastics, polymer and petrochemical industries, medical/biomedical industries, etc. and devices for measuring the viscosity of fluid have been in existence for many years. One common viscometer type is the oscillatory viscometer, which measures sample viscosity by determining the amount of damping experienced by a moving probe immersed in a sample fluid.

J. G. Woodward, a pioneer in the field, developed one of the first oscillatory viscometers in 1953 (*The Journal of the Acoustical Society of America*, 25, 147–151, 1953. Woodward measured the amount of damping experience by an oscillating plate immersed in a fluid, and developed a mathematical relationship between the damping and fluid viscosity. His calculations are still used today for oscillating probe viscometers.

Also in 1953, Roth and Richard described and later patented an apparatus and method for measuring the viscosity of fluid-like materials using an elongated strip of magnetorestrictive material vibrated at high frequency by transducer coils. See *J. Appl. Phys.*, vol. 24, no. 7, 1953 and U.S. Pat. No. 2,839,915, both incorporated herein by reference. In both references a solid rectangular strip was used as a sample probe which oscillated in the longitudinal compressional mode. In 1989, Portman (U.S. Pat. No. 4,799,378, incorporated herein by reference) disclosed a piezoelectric viscometer and used, as a viscosity probe, a quartz reed with a ball formed on the end thereof. The vibratory motion of the piezoelectric element caused the probe to oscillate. The Portman viscometer is a device wherein the viscosity probe's range of motion is approximately 1 mm or more, however, the measurement of viscosity in such a system depends upon viscous flow theory.

Several viscometers have been developed using probes which undergo a twist vibration (i.e., a torsional mode of vibration) about a central axis. Miura (U.S. Pat. No. 4,811,593, incorporated herein by reference), disclosed such an instrument in 1989 using a transmission shaft, via twist vibration, which detects the viscous resistance offered by a liquid sample. The Paar Physica U.S.A. Physica-Rheoswing commercial rheometer uses such torsional oscillations in determining dynamic and kinematic viscosity.

Harade, also in 1989, described a rotating viscometer wherein a rotary member spins within a fixed housing, causing the sample, for which the viscosity is being measured, to flow. See U.S. Pat. No. 4,811,593 which is also incorporated herein by reference. The Bohlin Visco 88 viscometer utilizes this general configuration by providing a rotating inner cylinder and a stationary outer cylinder.

However, even with this great diversity in viscometer design, no viscometer to date has successfully combined the attributes of simple design, portability, field toughness, low cost and accuracy. Portability and field toughness are particularly advantageous for applications which include the need to measure the viscosity of a sample outside of the laboratory setting, such as a viscosity of a drilling mud on an off-shore oil rig. Sending samples back and forth to a laboratory for a viscosity determination can be tedious and time-consuming, and can significantly slow down work already in progress. A viscometer must necessarily be accurate and low cost is also an obvious desirable feature. Current commercial available viscometers are expensive in that they range in cost from $7000 to $25,000.

SUMMARY OF THE INVENTION

Accordingly, one object of this invention is to provide an electronic viscometer which overcomes the drawbacks of the prior art by combining portability, low cost and accuracy.

Another object of the present invention is to provide a viscometer having a vibrating drive and a tubular probe.

Another object of the present invention is to provide an electronic viscometer that induces shear waves and a sample being measured with an oscillating probe set into oscillation by a piezoelectric drive.

Another object of the present invention is to provide a viscometer which determines the viscosity of liquid by providing a measurement of the product of absolute viscosity times density at temperature.

Another object of the present invention is to provide an electronic viscometer whose probe oscillates substantially in the axial mode, and most preferably in the axial mode only (motion along the long axis of the probe).

Another object of the present invention is to provide an electronic viscometer including circuitry for converting the viscosity density product into either density or absolute viscosity.

Another object is to provide a tubular viscosity probe having a sharp edge on the end which is to be immersed in a sample to have substantially viscous shear only and having a hole in the wall of the probe, located away from the end of the sharp edge and above the surface of the sample being measured and to allow the sample in the tube to reach the same level as a sample outside the tube.

It is another object of the present invention to achieve accuracy in viscosity measurement by circuitry which employs a phase locked loop circuit design in order to maintain precise phase relationship between a piezoelectric drive signal and a feedback signal and to provide that the probe is driven at probe and plate system resonant frequency.

BRIEF DESCRIPTION OF THE DRAWINGS

A more complete appreciation of the invention and many of the attendant advantages thereof will be readily obtained as the same becomes better understood by reference to the following detailed description when considered in connection with the accompanying drawings, wherein.

DESCRIPTION OF THE PREFERRED EMBODIMENTS

Figure 1:
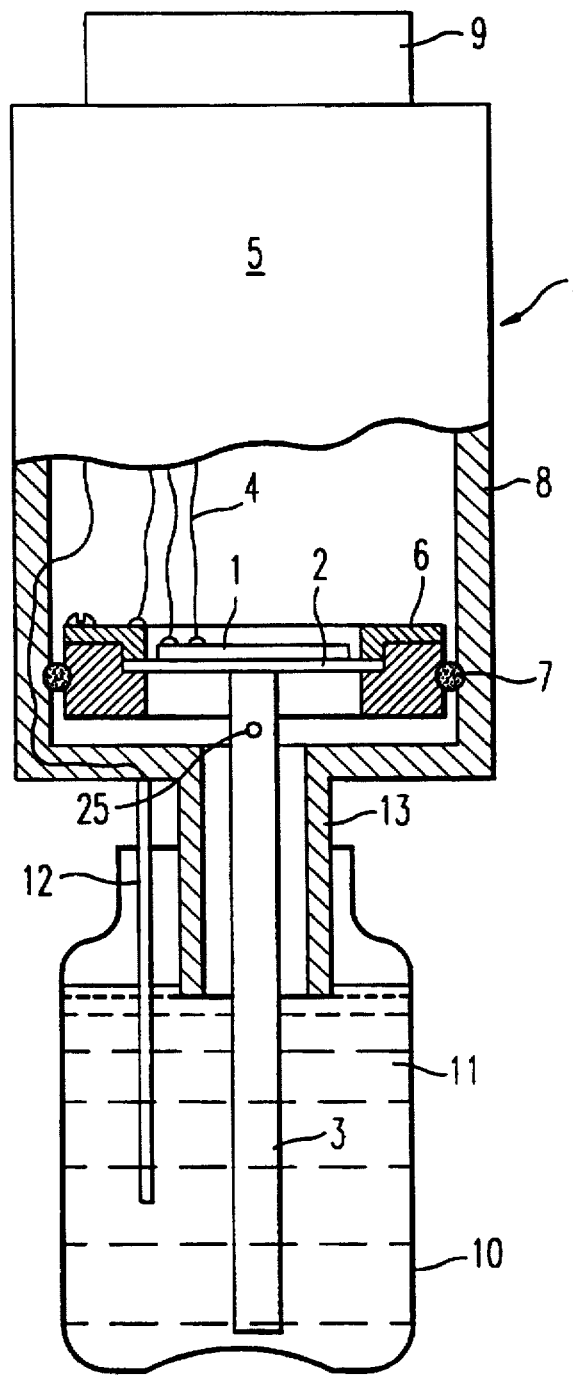
FIG. 1 is a view of a preferred electronic viscometer positioned to measure fluid in a container.

Referring now to the drawings, wherein like reference numerals designate identical or corresponding parts throughout the several views, and more particularly to FIG. 1 thereof, an electronic viscometer 20 is positioned inside of a bottle 10 containing a sample of fluid 11. The viscometer 20 utilizes a piezoelectric crystal 1 positioned on the plate 2 with a hollow tube 3 having a vent 25 near the top of the tube. The tube 3 is attached to the center of the plate 2 and is perpendicular thereto. The piezoelectric crystal surface is connected by wires to electronic components inside the housing 5 which supply oscillating voltage to drive the piezoelectric crystal. A metal holder 6 holds the plate 2 and is supported by O-ring 7. External housing 8 is positioned to retain the structure 9. A thermocouple 12 measures the sample temperature. The immersion control tube 13 controls the depth to which the tube 3 is immersed in the liquid 11.

Figure 2:
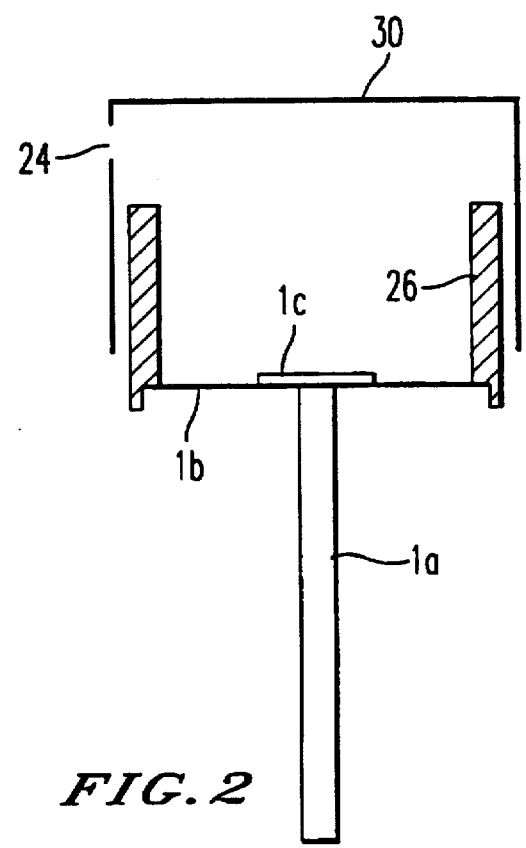
FIG. 2 is another embodiment of the electronic viscometer and particularly the structure and positioning of the probe assembly within the measuring device.

Another embodiment for the structure of the piezoelectric crystal and tube assembly is shown in FIG. 2 wherein the piezoelectric crystal 1c is positioned on a plate 1b which in turn is attached to the brass tube 26. Attached to the plate 1b, on a face opposite the piezoelectric crystal 1c, is the tube 1a. In the construction of FIG. 2 the probe assembly plate 1b has a O.D. of 1.38 inches while the brass tube has a O.D. of 1.5 inches. The plate 1b is soldered to the edge of the brass tube 26. A covering 30 provided with the port 24 covers the piezoelectric crystal and provides access to electronic components through the port 24. The electronic viscometer utilizes a vibrating drive which causes the viscosity probe to oscillate at a resonant frequency between 500 and 3000 Hz and preferably between 1,000 and 2,000 Hz at an amplitude ranging from $1 \times 10^{-4}$ to $1 \times 10^{-1}$ mm, and preferably 1 to $10 \times 10^{-3}$ in error. These ranges approach the probes resonant frequency. The damping of the oscillations of the viscosity probe due to the sample fluid being measured depends upon the wave mechanics (Erich, F. R., *Rheology Theory and Applications*, V. 3, Academic Press, 1960, pp. 65–70) rather than Newtonian Mechanics or Lambs' Plate Mechanics (Lamb, *Proc. Roy. Soc. A*, v. 98, p. 205, 1921), both references being incorporated herein by reference.

Figure 3:
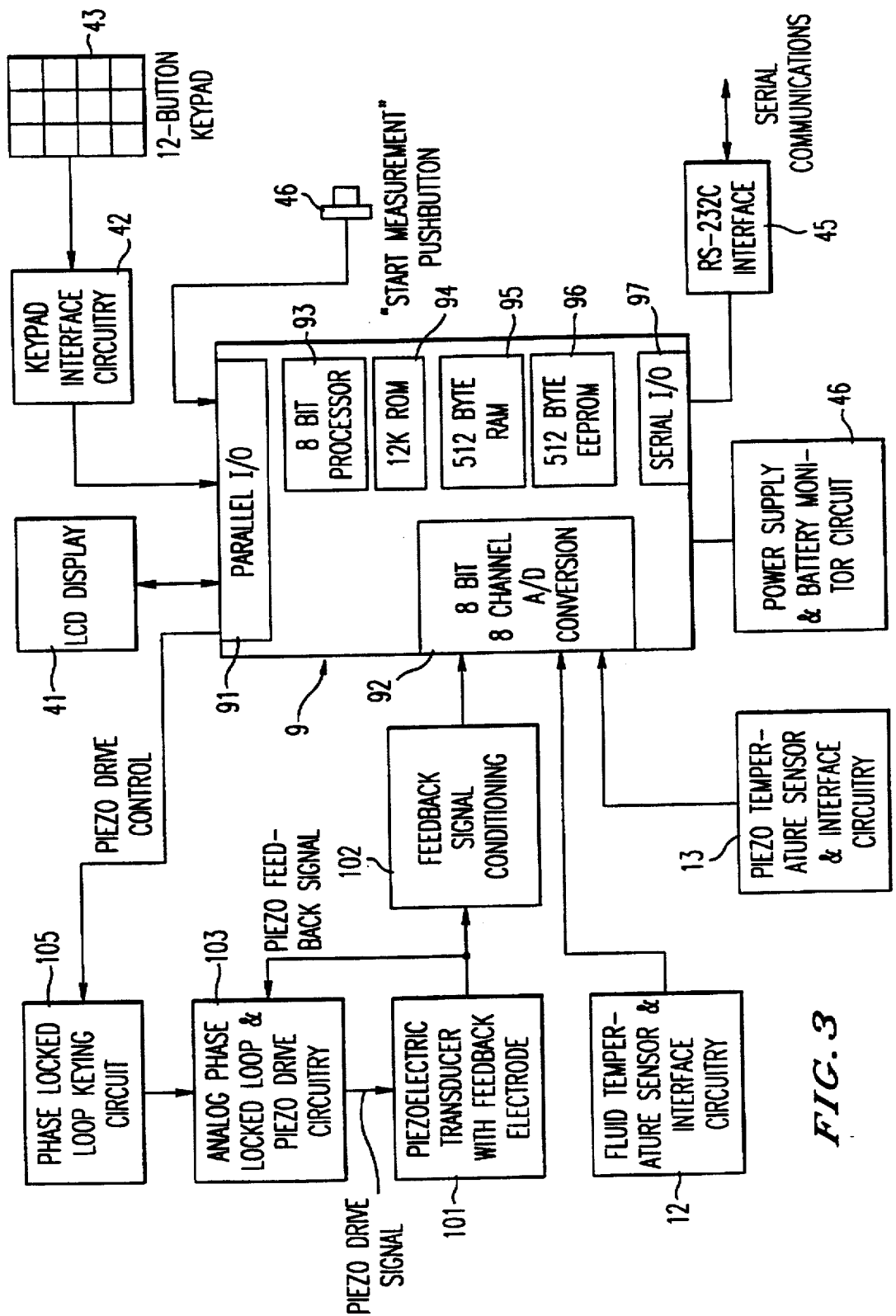
FIG. 3 is a block diagram illustrating microprocessor control of the piezoelectric viscometer of FIGS. 1 or 2.

Microprocessor control of the piezoelectric viscometer of either the embodiment of FIG. 1 or FIG. 2 is shown in block diagram form in FIG. 3. The computer 9 is typically an 8-bit microcontroller having an 8 bit 8 channel A/D (analog/digital) converter 92 as well as an 8 bit processor 93 and in the embodiment illustrated a 12K ROM with a 512 byte RAM 95 and a 512 byte EEPROM 96. A serial I/O 97 is connected to a RS-232C interface 45 to provide serial communication and a parallel I/O interface 91 is connected to a liquid crystal display 41 and to a key pad interface circuitry 42 for ultimate connection to a key pad 43 as well as a start push button 46. Also connected to the parallel input/output 91 is a piezo drive control fed to a phase locked loop keying circuit 105 which in turn is connected to an analog phase of the locked loop and piezo drive circuitry 103. The piezo drive circuitry provides a drive signal to the piezoelectric transducer which has a feedback connection to the drive circuitry 103. The feedback signal is also conditioned at 102 and fed to the A/D converter 92. Other measurements include the fluid temperature sensor and interface circuitry 12 and the piezo temperature sensor and interface circuitry 13 which are also fed to the A/D converter. The entire system is controlled by a power supply and battery monitor circuit 46.

The substances which can be used as the piezoelectric crystal include quartz, Rochelle salt and various piezoelectric ceramic. The piezoelectric drive is superior to other vibratory drives because these crystals, once subjected to mechanical stress, produce electric currents and when subjected to an AC electrical voltage the crystals vibrate.

In a preferred embodiment a 25 millimeter diameter piezoelectric crystal made of ceramic and sintered to a thin brass plate having a 35 mm diameter is used. A feedback electrode structure which resonates at 2.8 khz is utilized. Other piezoelectric materials useful for the present application vibrating drive include lithium niobate, and the piezoelectric materials in the "Piezoelectric Ceramics" by E. Kolm in *Mechanical Engineering*, February, 1984, page 43, incorporated herein by reference. Further examples of piezoelectric elements useful in the present invention as vibrating drive structure are described in Singman, *Popular Electronics*, page 69, March 1994 incorporated here by reference and U.S. Pat. Nos. 4,799,378, 4,994,703, 4,920, 787 and 4,811,593.

Various materials including the recited metal tube and metal plate system can be used for the viscometer plate and probe. In general, any combination of tube and plate system which satisfies a requirement for frequency in two separate modes of vibration can be used. The first vibration mode is the lateral vibration mode of a tube due to a sinusoidal deflection of the plate which is given by the equation:

$$f_A = (1/2\pi)[(3E_p t_p^3)/(\alpha u_t L_t^3)]^{1/2} \qquad \text{Equation 1}$$

Where:

$E_p$ = the modulus of elasticity of the plate, psi
$t_p$ = thickness of plate, in
$u_t$ = mass per unit length of tube, lbs-sec²/in²
$L_t$ = probe length, in
$\alpha$ = 0.5 to 0.6.

This natural frequency $f_A$ of the plate and tube must be much less than the driving frequency which is approximately 1.5 kHz. The basic equation is derived from W. C. Young, "Roark's Formulas for Stress and Strain," McGraw-Hill, 6th Ed. p. 434 using the equation for a "trunnion support of the tube on the plate".

The second mode of vibration which must be met is the lateral vibration of the tube as a cantilever beam for which the first natural frequency of transverse or bending vibration must be well below the resonant frequency of the system and avoid coupling with any higher order natural transverse frequency of the system. This first natural transverse frequency is given by:

$$f_B = (3.52/2\pi)[E_t I_t/u_t L_t^4]^{1/2} \qquad \text{Equation 2}$$

where $I_t$ = the moment of inertia of the tube, in⁴.

This equation is derived from Den Hartog, "Mechanical Vibrations," McGraw-Hill, 1956.

For the preferred embodiment, the value $f_A = 96$ HZ and $f_B = 1200$ Hz which is, in both modes of vibrations, well below the driving or resonant frequency of the plate and tube which is 1.5 kHz.

Any material combination for the plate and the tube which allow the conditions for $f_A$ and $f_B$ to be less than 1.5 kHz may be used.

The vibrating drive of the electronic viscometer is capable of imparting substantially the pure axial motion to the viscosity probe at the natural frequency of the motion (e.g., 1.5 kHz) along a long axis of the probe. An AC feedback voltage is used to calculate the product of the viscosity and the density.

The viscosity probe is formed by that portion of the probe which is inserted into the sample being measured such samples are preferably fluids or fluid-like samples including paint, oil, water etc. In one embodiment the viscosity probe has a long axis and is a hollow tube having a circular cross-section, and a longitudinal axis with an aspect ratio (length divided by outside diameter) of from 1.5 to 15, preferably 10 to 13, and more preferably 10.2 to 11. The thickness of the tubular wall is preferably uniform and is from 0.005 to 0.035 inches thick, preferably 0.010 to 0.015 inches thick. Regardless of the probe shape cross-section it is preferred to have one long axis only and it is preferred that it is capable of being described by an overall aspect ratio (long axis divided by shortest axis). The wall at the end portion of the probe which is to be inserted into a sample to provide viscosity measurement is preferably tapered or sharpened (pointed) in order to reduce compression effects and maximize shear forces produced by pure or substantially pure axial probe motion (i.e., a motion wherein the tube vibrates or oscillates along only its long axis in a piston-like motion, the end of the tube remaining in the sample throughout the measurement).

If a hollow viscosity probe is used, it may include within its walls at least one vent hole in any shape including the shape of a circle, square etc., which allows the escape of trapped air when one end of the probe is inserted into a fluid or fluid-like sample. Utilizing the vent hole, the sample is able to rise up within the probe to the same or approximately the same sample level as is present along the outside wall of the probe. Preferred probe inner diameters range from 0.189 inches to 0.25 inches, preferably 0.19 to 0.22 inches with the preferred probe length ranging from 2.3 to 3.0 inches and preferably 2.5 to 2.75 inches.

The material of the viscosity probe may be plastic, metal, ceramic etc. Metal tubes are preferred and any material which can maintain a tubular shape and be driven in a pure or substantially pure axial motion within the frequency and amplitude ranges described above may be utilized. If a hollow probe is used the shape may include square, rectangular, triangle, oval, etc., cross-sections. Each probe has the longitudinal axis and, if a hollow probe is used, an inside and outside surface for contact with the sample to be measured.

To increase accuracy, it is preferred that the viscometer of the present invention have heating/cooling means capable of providing the drive and probe at substantially the same temperature (±10 degrees, preferably 13 degrees or less), and preferably at the temperature of the sample being measured. Examples of such heating/cooling means includes heat pumps, refrigeration units, resistance heaters, fans etc.

The viscosity probe is connected to the vibration drive circuitry as illustrated in FIG. 3 or by any other means which provides for vibration transferring attenuating or amplifying of the signals.

The circuitry of FIG. 3 provides for a driving of the vibrating crystal at a constant or approximately constant voltage with the drive circuit providing a square wave to the piezoelectric crystal which, in turn, provides a constant driving force to the viscosity probe. A sinusoidal feedback voltage is generated by the feedback 102 with this feedback voltage being a measure of the amplitude of the viscosity probe. The ratio of amplitudes of the viscosity probe measured in air (essentially undamped) to the amplitudes measured when inserted in a fluid sample of interest provides a measure of damping which can be used to calculate the product of absolute viscosity and density. That is, the damping of the viscometer when placed in a sample being measured is proportional to the feedback voltage of the vibrating drive which is preferably a piezoelectric crystal. The circuit is self-oscillating.

In addition to measuring the amplitude of vibration and subsequent damping in a sample to be measured, the absolute viscosity and density product of the sample may be obtained by measuring the phase shift of the drive input and output signal as illustrated in U.S. Pat. No. 4,922,745.

The electronic block diagram of FIG. 3 provides information to the microprocessor 9 which calculates the absolute viscosity and density product according to the following formula:

$$\eta \rho = K(f_{air}/f)[(f_{air} Y_{air}/fY) - 1]^2 \qquad \text{Equation 3}$$

where:
η=the absolute viscosity
ρ=the density or specific gravity
K=a constant for the instrument
$f_{air}$=the resonant frequency with the probe in air
f—resonant frequency with the probe in the sample
$Y_{air}$=the resonant amplitude with the probe in air
Y=the resonant amplitude with the probe in the sample The electronic viscometer may be contained within the housing and isolated by springs or a O-ring or a rubber gasket. The housing may include an immersion control tube through which the viscosity probe exits the housing with the length of the immersion control tube being chosen so that when the electronic viscometer is immersed in a sample up to the end of the immersion control tube, the viscosity probe which extends beyond the immersion control tube is inserted into the sample for a desired depth as indicated in FIG. 1. If such a tube is not used, a simple mark on the probe may be utilized. The electronic components may be contained in the viscometer housing or in a separate area connected to the viscometer probe by wires, etc.

Figure 4:
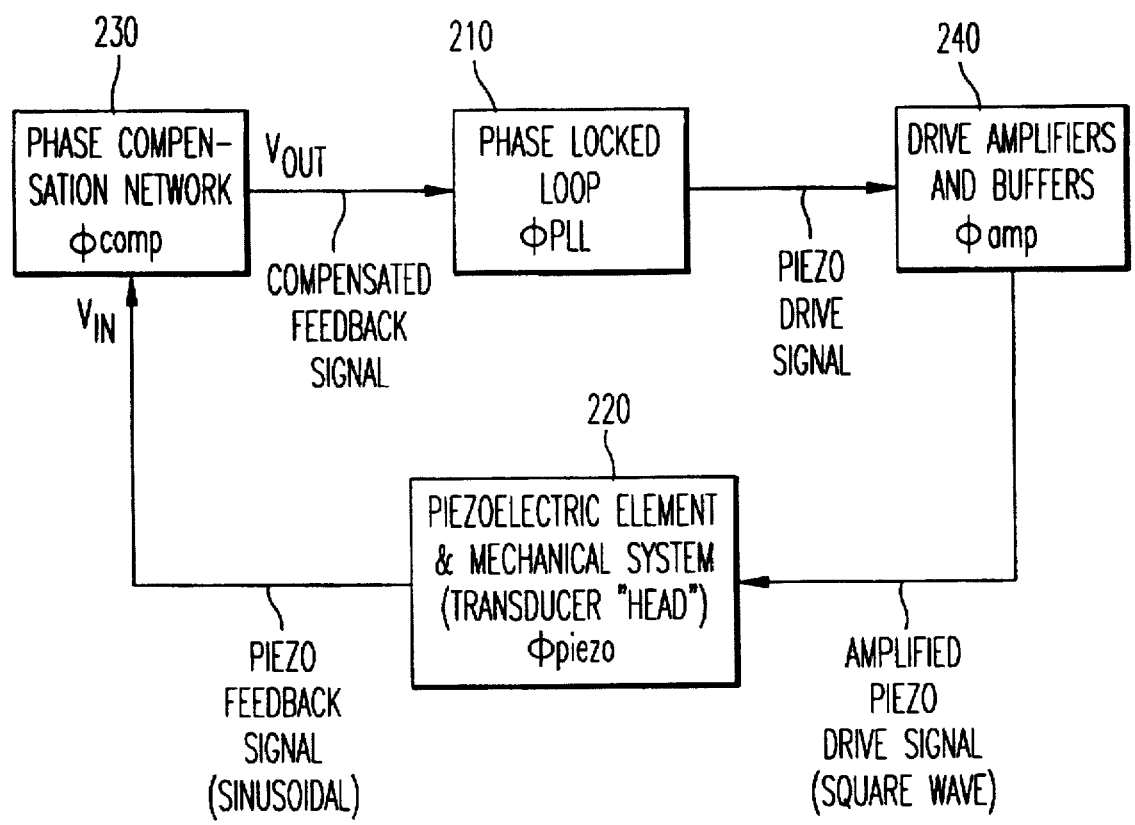
FIG. 4 is a preferred embodiment for phase locked loop design to provide that the probe of FIG. 1 or 2 is driven at resonant frequency.

Another embodiment for the feedback circuitry of FIG. 3 is detailed in FIG. 4 which provides that the piezoelectric element is driven at its resonant frequency by a square waveform with a 50% duty cycle and no direct current component. A resonant frequency will vary by approximately plus or minus 2% depending upon the viscosity of the sample being measured within a range of from 0 to 5000 centipoise. Additionally, a precise phase relationship between the piezoelectric elements drive and the feedback signals $\phi_{piezo}$ must be maintained. The phase relationship is an inherent characteristic of the piezoelectric element and the mechanical system and is a constant provided the element is driven at resonance. Experimental data shows that the feedback signal generated by a piezoelectric element lags the driving signal by approximately 270° when driven at resonance.

The FIG. 4 system provides both resonant frequency as well as signal phase requirements. The piezoelectric viscometers phase locked loop (PLL) 210 provides a piezo drive signal which is equal in frequency to the phase compensated feedback signal produced by the piezoelectric element 220 thus satisfying the resonant frequency requirements of the system. This requirement is satisfied provided that the feedback signal is within the specified lock and capture ranges of the PLL. The signal phase requirements of the system are satisfied by the phase compensation network 230 which is a first order passive high pass filter which introduces a phase shift to the piezo element control loop $\phi_{comp}$ such that the required phase relationship between the piezoelectric elements drive and the feedback signals $\phi_{piezo}$ is maintained. This relationship is expressed in equation 2 where $\phi_{PLL}$ and $\phi_{amp}$ are phase shifts introduced into the piezoelectric element controller by PLL and the drive amplifiers 240 respectively. Phase shifts $\phi_{PLL}$, $\phi_{amp}$ and $\phi_{comp}$ are essentially constant over the narrow resonant frequency range of the piezo element and mechanical system.

$$\phi_{com} = \phi_{piezo} - (\phi_{PLL} + \phi_{amp})$$ Equation 4

The transfer function for the phase compensation network 230 is a first order passive high pass filter and is expressed in equation 3. The resistive and capacitive components of the phase composition network are R and C respectively. When this transfer function is evaluated for particular values of R and C, at its lower 3 db point where $V_{out}/V_{in} = 0.707$ yields the networks lower cut off frequency $\omega_c$ expressed in radians.

$$V_{out}/V_{in} = R/(1/\omega + R)$$ Equation 5

The phase compensation network 230 provides phase shift which is directly related to the ratio of its lower cut off frequency $\omega_c$ and the resonant frequency of the piezoelectric element and mechanical system $\omega$ as shown in equation 4.

$$\phi_{comp} = (\pi/2) - \arctan(\omega/\omega_c)$$ Equation 6

$\phi_{comp}$ can be controlled using the equations 1–3 and appropriate values of R and C so that the required phase relationship between the piezoelectric elements drive and feedback signal $\phi_{piezo}$ is maintained which is essential for accurate viscosity measurement.

Obviously, numerous modifications and variations of the present invention are possible in light of the above teachings. It is therefore to be understood that within the scope of the appended claims, the invention may be practiced otherwise than as specifically described herein.

What is claimed as new and desired to be secured by Letters Patent of the United States is:

1. An electronic viscometer, comprising:

a piezoelectric crystal attached to a first side of a metal plate;

a hollow circular tube having a first end attached to a second side of said plate, said tube having a longitudinal axis perpendicular to said second side;

said piezoelectric crystal being driven by a piezoelectric drive means having a feedback electrode for providing a feedback signal, wherein said piezoelectric drive means includes a phase compensation network receiving a feedback signal from said feedback electrode and providing a compensated feedback signal to a phase locked loop and wherein said phase locked loop provides a piezoelectric drive signal having the same frequency as a frequency of said phase compensated feedback signal and wherein said piezoelectric crystal receives said piezoelectric drive signal as an input signal and outputs an exclusive longitudinal vibratory motion at resonance to said tube, said tube having at least a second end which has a sufficiently thin wall to maximize shear forces produced by said exclusive longitudinal vibratory motion when said second end is inserted in a liquid whose viscosity is to be measured and wherein said tube has an aspect ratio chosen so that said tube provides said exclusive longitudinal vibratory motion when said piezoelectric drive signal is an oscillating constant root means square value driving voltage.

2. The viscometer as claimed in claim 1 wherein said drive means further includes an amplifier means for amplifying said piezoelectric drive signal and wherein said piezoelectric drive signal is a square wave.

3. The viscometer as claimed in claim 1 wherein said aspect ratio is between 1.5 and 15.

4. The viscometer as claimed in claim 1 wherein said tube includes an air vent which allows for the escape of trapped air when said one end of said tube is inserted into said fluid.

5. The viscometer according to claim 1, wherein said tube oscillates at a frequency of from 500 to 3000 Hz.

6. The viscometer according to claim 1, wherein said frequency is between 1 and 2 KHz.

7. The viscometer according to claim 1, further including temperature measurement means for providing said piezoelectric crystal at substantially the same temperature as said fluid whose viscosity is being measured.

8. An electronic viscometer, comprising:

a piezoelectric crystal attached to a first side of a metal plate;

a hollow circular tube having a first end attached to a second side of said plate, said tube having a longitudinal axis perpendicular to said second side;

said piezoelectric crystal being driven at a first frequency and outputing an exclusive longitudinal vibratory motion at resonance to said tube, said tube having at least a second end which has a sufficiently thin wall to maximize shear forces produced by said exclusive longitudinal vibratory motion when said second end is inserted in a liquid whose viscosity is to be measured and wherein said tube has an aspect ratio chosen so that said tube provides said exclusive longitudinal vibratory motion when said piezoelectric drive signal at said first frequency is an oscillating constant root means square value of driving voltage;

said tube and plate system having at least a first and a second mode of vibration wherein said first mode of vibration is a lateral vibration mode of said tube due to a sinusoidal deflection of said plate and wherein said second mode of vibration is a lateral vibration of the tube as a cantilever beam having a first natural frequency of transverse or bending vibration and wherein said first vibration mode and second vibration mode each have a frequency less than said first frequency.

* * * * *